(12) United States Patent
Albani

(10) Patent No.: US 10,327,943 B2
(45) Date of Patent: Jun. 25, 2019

(54) DEVICE OF CONTRAST OF GASTROESOPHAGEAL REFLUX IN CHILDREN

(75) Inventor: Roberto Albani, Rome (IT)

(73) Assignee: DR ALBANI LIMITED, London (GB)

( * ) Notice: Subject to any disclaimer, the term of this patent is extended or adjusted under 35 U.S.C. 154(b) by 329 days.

(21) Appl. No.: 14/343,689

(22) PCT Filed: Jul. 13, 2012

(86) PCT No.: PCT/IB2012/053592
§ 371 (c)(1),
(2), (4) Date: May 1, 2014

(87) PCT Pub. No.: WO2013/054210
PCT Pub. Date: Apr. 18, 2013

(65) Prior Publication Data
US 2015/0027449 A1    Jan. 29, 2015

(51) Int. Cl.
*A61F 5/37*    (2006.01)

(52) U.S. Cl.
CPC .................................. *A61F 5/3784* (2013.01)

(58) Field of Classification Search
CPC ..... A47D 13/08; A47D 13/025; A61F 5/3784; A61G 2200/14; A61G 1/017; A61G 5/00; A61G 7/005; B62B 7/12; B62B 9/104; B60N 2/2848
USPC .................. 5/603, 655; 280/30, 47.25, 648; 297/130, 377, 467, 466, 468; 128/870, 128/871, 873; D6/333; D12/129
See application file for complete search history.

(56) References Cited

U.S. PATENT DOCUMENTS

| | | | | |
|---|---|---|---|---|
| 3,431,020 A | * | 3/1969 | Tyndall ................ | A47D 13/025 297/377 |
| 3,563,601 A | * | 2/1971 | Dickey ................. | A61F 5/0193 280/47.25 |
| 4,359,045 A | * | 11/1982 | Cozzi ..................... | A47D 1/002 297/354.13 |
| 4,398,748 A | * | 8/1983 | Duvignacq ............... | B62B 7/08 280/644 |
| 4,873,735 A | * | 10/1989 | Fermaglich .............. | A47D 1/00 5/655 |
| 2005/0028286 A1 | | 2/2005 | Smart | |
| 2008/0029103 A1 | | 2/2008 | Regev et al. | |

* cited by examiner

*Primary Examiner* — Ophelia A Hawthorne
*Assistant Examiner* — Caitlin A Carreiro
(74) *Attorney, Agent, or Firm* — Stephen Kenny; Peter Sullivan; Foley Hoag LLP

(57) ABSTRACT

A device (10) for counteracting gastroesophageal reflux in babies, including at least a flat rigid support (12), with a supporting side covered with stuffing or a cushion (11). The device includes mechanisms of assemblage (19) with a frame (30, 30') including wheels. The supporting side of the rigid support has an inclination of 70-90° compared to the horizontal. The device also includes a sling (13) coupled with the rigid support (12) and fitted on the supporting side for placing and securing a baby (20) with his abdomen facing the cushion, in the space between the cushion and the sling. The sling includes a back rest (15) inclined in the same direction of the rigid support (12) and having an upper extremity higher than an upper extremity of the rigid support (12) and the cushion (11).

19 Claims, 2 Drawing Sheets

Figures 4, 5:
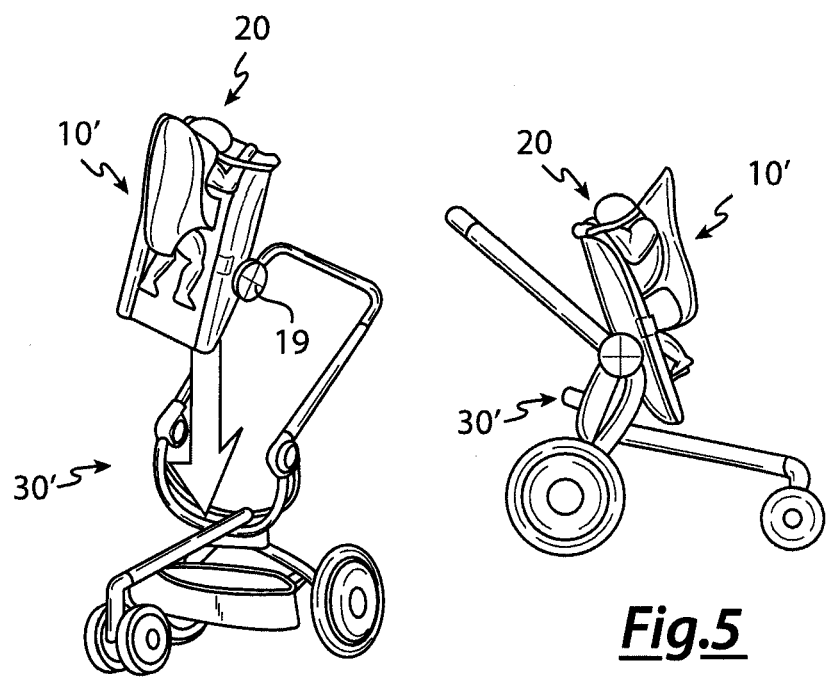

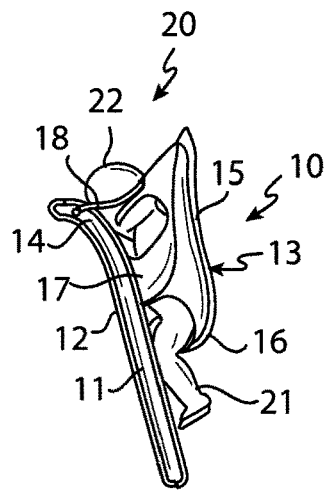
*Fig.1*
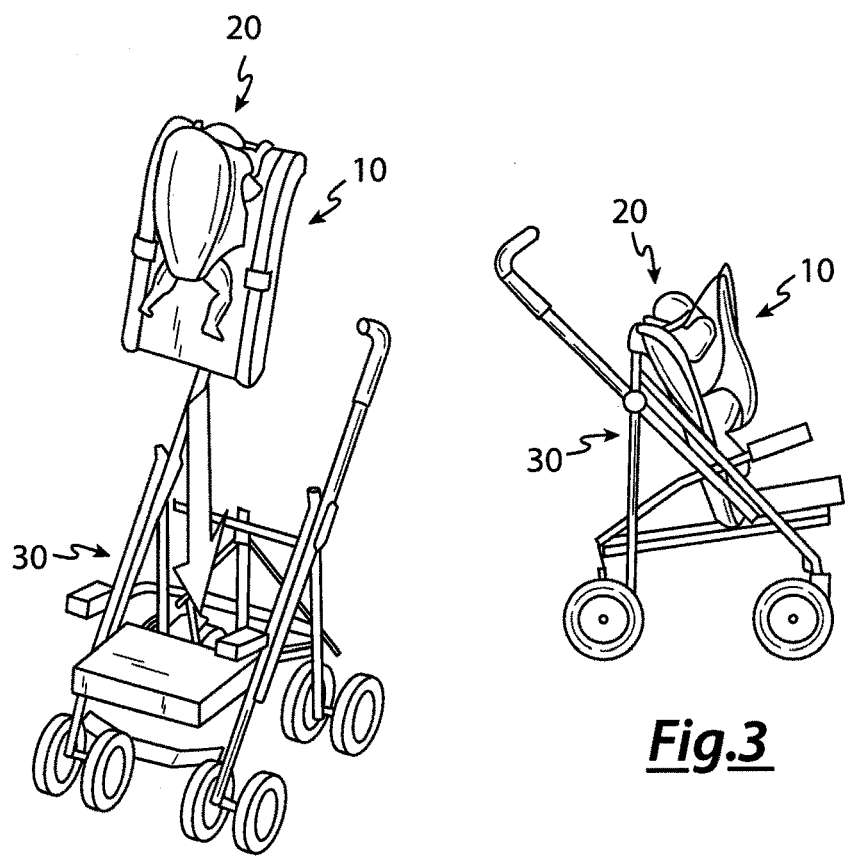
*Fig.2*
*Fig.3*

DEVICE OF CONTRAST OF GASTROESOPHAGEAL REFLUX IN CHILDREN

The invention in question is a device that is able to counteract gastroesofageal reflux in infants.

It is well known that gastroesphageal reflux is a very common occurrence in infants.

It is defined as the frequent passage of gastric content into the esophagus, due to the malfunction of a valve, the lower esophageal sphincter (cardia), which normally prevents the contents of the stomach from returning upwards.

Therefore, the milk acidified by gastric juices is regurgitated continually from the stomach toward the esophagus.

The esophagus, being under constant attack of gastric acid, becomes inflamed.

In other words the baby ends up getting esophagitis, which brings him/her a range of discomforts.

Esophagitis causes a burning sensation, which triggers constant restlessness, great difficulty in going to sleep and in resting without interruption.

The continuous "rumination" of gastric material that goes up during the interval between feedings, implies the swallowing of large quantities of air, that accumulates in the stomach first and then in the bowel, thus contributing to the baby's suffering and causing colic and troublesome feedings.

Furthermore, the inflamed esophagus goes often into a spasm, which causes very intense pain.

Finally, esophagitis also causes frequent and prolonged hiccups, which occur practically after every feeding.

There are other consequences of this disorder. It can even trigger episodes of choking and, on rare occasions, pulmonary infections due to inhalation of gastric contents.

Given the relevance of this disorder, many doctors, health workers in general and even parents have been long searching for a remedy that would allow children affected by gastroesophageal reflux to regurgitate less, swallow less air and enjoy better rest.

In every case, the proposed solutions originated from the observation that babies affected by this disturbance prefer to keep their torso in the near vertical position. In this way they prevent or diminish the backlash of stomach content upwards. Actually, the affected baby likes being held against his/her parent's chest, with his/her head leaning over parent's shoulder for at least half an hour to an hour after feeding. In this position the baby can belch more easily and can reduce regurgitation substantially.

So much so that this way he/she can go to sleep more quickly and remain asleep. However he/she becomes restless and wakes up crying as soon as he/she is put in a sitting or lying position, which will usually force parents to pick him/her up and place him/her back in the preferred position.

The solutions that have been proposed until now to relieve the baby's suffering from reflux have all been made in the form of cushions or seats, with the surface on which the baby's back is placed inclined at an angle of approximately 30-40° over the horizontal line, therefore representing a simple evolution of the traditional practice of placing cushions or books under the head of the crib mattress.

According to the U.S. Pat. No. 7,003,831, the inventor proposes a cushion with the surface for placing the baby inclined at approximately 30° from the supporting surface on the floor, including a sling which prevents the baby from sliding down, ending up on the floor, in the horizontal position.

However, the sitting position, although it gives some relief to the baby's discomfort and helps him/her to sleep better, it is not ideal especially in the hour immediately after feeding. This is because in this position the baby cannot easily belch. It is also because, every time he/she bends his/her torso forward, the pressure on his/her stomach increases and worsens the tendency to regurgitate.

An attempt to simulate the position on parent's shoulders is described in U.S. Pat. No. 6,931,683, a wedge cushion that can be used in two positions: in the first position, the surface of the cushion facing upwards (apt for the placement of the baby) is on an inclination of a maximum of 15-45° compared to the supporting surface on the floor, on which the cushion is positioned. The placement surface is particularly suitable to hold the baby, tummy down, in a similar position to that on parent's shoulder; in a second position, instead, the surface of the cushion facing up (on which the baby has to be placed) is the opposite of the previous one and it is likewise at an angle of 15-45° compared to the floor, presenting a concave area to better hold the baby face up. In addition, the U.S. Pat. No. 7,251,846, describes a sling devised to hold a baby on the cushion which is described in U.S. Pat. No. 6,931,683.

In synthesis, U.S. Pat. No. 6,931,683 describes a bulky cushion with double use which, in one of the uses, allows the baby to lay face down on a surface at 15-45°, preferably 30-40°, always held by a sling to prevent him/her from sliding downwards. Although this solution partially simulates the preferred position of the baby with reflux, it has three fundamental flaws:

its inclination is very far from the vertical and therefore does not allow the baby to easily belch and reduce regurgitation as happens in the position on parent's chest.

It is an object to be kept on the floor, which makes it awkward to move around with the baby on it; and finally if the baby goes to sleep on it, he/she is still very close to the prone position (30-40°), which currently is strongly advised against for its proven association with "crib death" (SIDS).

In light of the above, it seems evident that there is a need for a new device. One different from the devices according to the prior art, that could eliminate all the flaws of the preceding objects and offer parents of babies affected by reflux decisive help to alleviate their children's suffering and improve the quality of life of the entire family.

In this context it is introduced the solution according to the present invention, with the purpose of supplying a device to counteract gastroesophageal reflux in babies, with a support surface on which the baby lies with his/her tummy, at an angle of 70-90 degrees compared to the floor, preferably 75-80°, i.e. at exactly the same inclination of the position on parent's chest. This surface has the upper extremity slightly curved, so as to make a smaller angle compared to the floor, ending up parallel to the floor, i.e. like the upper part of parent's shoulder, to offer support for the baby's head. The device includes also a harness in the shape of a sling, to hold the baby attached to the supporting surface. In order to ensure that the head of the baby, whose neck muscle are not well developed yet, does not loll backwards, the back rest of the sling is higher than the supporting surface. It also includes a supporting structure with wheels, like a stroller, to easily move the baby around.

This particular device allows to counteract gastroesophageal reflux more effectively than the devices according to the known technique, especially because of the inclination at 70-80°, preferably 75-80°, compared to the horizontal, at which the baby is placed with his/her tummy against the cushion, supported by the sling.

In addition, the device according to the present invention makes it possible to move the baby on wheels, without having to pick him/her up manually, as in the case of U.S. Pat. No. 6,931,683.

Therefore, the scope of the present invention is to produce a device for counteracting gastroesophageal reflux in babies, which would overcome the flaws of the solutions according to the known technology and to attain the technical results aforementioned and described.

A further scope of the invention is that the said device may be manufactured at substantially low costs for what concerns production and management costs.

Last but not least scope of the invention is to create a device to counteract gastroesophageal reflux in babies, which is simple, safe and reliable.

Therefore, the aim of the present invention is to supply a device to counteract gastroesophageal reflux in babies, including at least a flat rigid support, with a placement side covered by a stuffing or cushion, equipped with mechanisms to associate it with a frame on wheels. The supporting side of said rigid support presents an inclination of 70-90° compared to the horizontal line and includes a sling, tied to said rigid support and fitted on said supporting side to place and hold a baby in the space between said cushion and said sling. Said sling includes a back support that has the same inclination of said rigid support and has its upper extremity higher than the upper extremity of said rigid support and said cushion.

In particular, according to the invention, the upper portion of the supporting side of said rigid support and of said cushion is curved to a position inclined by at least 30° compared to the remaining part of the supporting side of said rigid support and of said cushion, preferably reaching the horizontal position.

Preferably, according to the invention, through the combination with said frame equipped with wheels, said supporting side of said rigid support and of said cushion, will assume an inclination of 75-80° over the horizontal line.

In particular, according to the present invention, said frame is the frame of a stroller.

The present invention will now be described, only by way of example, and not restrictively, according to a preferable form of production, with special reference to the attached drawings in which:

FIG. 1 shows a side view of a device to counteract gastroesophageal reflux in babies according to a first embodiment of the present invention and of a baby placed in it, FIG. 2 shows a prospective view of the device in FIG. 1 and of the frame of a first stroller, on which the device is being applied, FIG. 3 shows a side view of the device in FIG. 1 applied to the frame of FIG. 2, FIG. 4 shows a prospective view of a device to counteract gastroesophageal reflux in babies according to a second embodiment of the present invention and of a baby placed in it and of the frame of a second type of stroller, on which the cushion is being applied, and FIG. 5 shows a side view of the cushion of FIG. 4 applied to the frame of FIG. 4.

Referring to FIG. 1, the device to counteract gastroesophageal reflux in babies according to the present invention is on the whole indicated with the reference number 10 and includes a cushion 11, with a rigid support 12, to which a sling 13 is attached, for the placement and securing of a baby 20, with his/her abdomen facing the cushion 11, in the space included between said cushion 11 and said sling 13, coupled through specific mechanisms to a stroller, mechanisms which guarantee an angle of the cushion itself 11 between 70 and 90 degrees, preferably between 75 and 80° compared to the horizontal. The combination with the structure of a stroller, of any form or weight, allows the device to keep its effective position, with the cushion 11 at an angle of 70-90° compared to the horizontal, besides guaranteeing its stability and the ease of mobility.

The superior portion 14 (approximately 5-7 cm) of the cushion 11 is curved over the rest of the cushion 11 and forms a support surface that is practically horizontal.

The sling 13 includes a back rest 15. In order to support the baby's 20 head 22 in case it lolls backwards, the superior extremity of the back rest is higher than the superior extremity of the cushion 11 and has the same inclination of the cushion 11. The sling also includes a lower portion 16, tied to the cushion 11, to support the bottom of the baby 20, side bands 17, on both sides of the central portion of the back rest 15, which are tied to the cushion 11 at a sufficient distance from the lower portion 16, so as to allow the passage of the baby's legs 21 between the lower portion 16 and the side bands 17.

In addition, small bands 18 are applied to both sides of the upper part of the back rest 15. These bands can be tied to and untied from the superior portion of the cushion 11, so as to allow an easier placement of the baby 20 in the space between the cushion 11 and the sling 13 when the small bands are untied and the back rest 15 is folded outwards. It has to be defined the maximum distance of the back rest 15 from the cushion 11, when the little bands 18 are attached to the cushion 11. Between the larger side bands 17 and the little bands 18 there has to be sufficient room to allow the passage of the baby's 20 arms.

Referring to FIGS. 2 and 3, the device 10 according to the prototype of the present invention already shown in FIG. 1, is seen combined with the structure 30 of a first type of stroller, while FIGS. 4 and 5, illustrate a variant of the device 10, combined with the structure 30' of a second type of stroller.

The baby 20 is secured in the sling 13 and well supported by it, with his/her abdomen facing the cushion 11 and the head leaning over the curved superior portion 14 of the cushion 11 itself, in exactly the baby's preferred position, i.e. in a position altogether similar to the one against the parent's chest and with his/her head leaning over parent's shoulder. This position allows the baby to belch easily and minimize regurgitation, as previously explained, and also allows him/her to go to sleep and stay asleep even for a long period, without any risk of suffocating, contrary to when he/she sleeps tummy down in a horizontal position or at an angle of 30-40° (as in the device of U.S. Pat. No. 6,931,683).

The elevated position of a baby placed on the device-stroller to counteract gastroesophageal reflux according to the present invention also allows the baby to look around without obstacles in front of his/her eyes, which amuses and relaxes him/her.

The height of the back rest 15 has to be superior to the one of the cushion 11, or, in any case, adjustable so as to exceed the height of the head 22 of the baby 20 and prevent it from lolling backwards.

In addition, the back rest 15 has to have the same inclination of the cushion 11, to keep the head of the baby steadily near the cushion itself and prevent it from lolling backwards 22.

The sling 13 has to be equipped with mechanisms to adjust its height and width, so as to follow the increasing measurements of the baby as he/she grows older. Alternatively, one can supply accessory slings of growing sizes for babies of different ages.

After six months of age, the superior part of the back rest 15 can be folded down and back or eliminated altogether, so that the baby can be put in the device and carried around facing outwards, as it is usually done when parents carry the baby with the sling tied to their chest.

The use of the device to counteract gastroesophageal reflux in babies according to the present invention does not exclude that the stroller be equipped with a capote and/or with a plastic cover to protect the baby from sun and rain.

To increase the baby's impression of being held on mother's chest it is possible to add inside the superior, curved, portion 14 of the cushion 11, where the baby rests his/her head, an audio device to reproduce music or the recording of mother's voice and/or heart beat.

Finally, it is also possible to add under the cushion 11 a vibrator (which simulates the sound and movement of a car) to lull the baby to sleep more easily.

From what we have said so far, it is clear that the solution according to the present invention allows to reach the expected aims without any risks to the health or life of the baby.

In conclusion, the device to counteract gastroesophageal reflux in babies according to the present invention allows parents to keep their baby in the ideal position after feeding and for all the desired time, eliminating the need to carry him/her in their arms for a lengthy time, as it usually happens with babies that are affected by reflux. Tests done with many such babies have shown that, even immediately after feeding, they adapt with evident signs of relief to the special stroller and stay on it for extended periods without complaint (while they would protest vociferously if put sitting or lying down). The baby almost always falls asleep on the device, and stays quiet for all the time so far experimented, i.e. up to an hour.

For the very fact that it is equipped with wheels, the device 10 to counteract gastroesophageal reflux in babies according to the present invention allows the adult to carry the baby around in the ideal position for the baby and at the same time look into his/her face at a close distance, contrary to what happens when the baby is lying in a carriage or sitting in a stroller according to the known technique.

In addition, tests done have shown that some of the advantages that this device offers babies affected by gastroesophageal reflux can be extended to all babies. In fact all babies prefer being held in the described position after feeding and when they are carried around. This consideration suggests that this device to counteract gastroesophageal reflux in babies according to the present invention may be proposed as a valid help to manage the after feeding period and the stroll out of the house for any child, newborn or baby, even when perfectly healthy.

The present invention has been described by way of example, and without restrictions, according to its preferable forms of production, but it has to be understood that variations and/or modifications may be made by experts in the field, without this way avoiding the relative field of protection, as defined in the attached claims.

The invention claimed is:

1. A device to counteract gastroesophageal reflux in babies, said device including:
   at least a flat rigid support including a supporting side covered with a cushioning material, the flat rigid support having a top and bottom defining a length therebetween and a mechanism adapted for coupling said flat rigid support with a frame having wheels, wherein, when said flat rigid support is coupled to said frame having wheels, the supporting side of said flat rigid support is inclined at 75-90° compared to the horizontal,
   a sling coupled to said flat rigid support and defining a space therefrom, said sling adapted to secure a baby placed in said space with his/her abdomen facing the cushioning material, said sling being a single unitary piece including a lower portion coupled to said flat rigid support proximate a midpoint of the cushion material, which is adapted, in use, to extend between the legs of a baby to form a seat which encloses and supports a bottom of the baby, and a back rest extending upward from the lower portion to the area of the baby's head,
   side bands located on either side of a central portion of said backrest, said side bands extending from said sling and removably tied to said flat rigid support at a location spaced from said lower portion of said sling;
   upper bands located on either side of an upper portion of said backrest, said upper bands having a first end extending from said sling and a second end removably tied to said flat rigid support at a location spaced from said lower portion of said sling; and
   wherein said back rest is inclined in the same direction of the flat rigid support and an upper extremity of said back rest is higher than an upper extremity of said flat rigid support and said cushioning material, and
   wherein said lower portion is tied to said flat rigid support to define said space between said sling and said flat rigid support.

2. The device according to claim 1, characterized in that a superior portion of the supporting side of said flat rigid support and of said cushioning material is angled relative to a remainder of said supporting side of said flat rigid support and said cushioning material by at least 30°, such that said superior portion is inclined at 45-60° compared to the horizontal.

3. The device according to claim 2, characterized in that said superior portion of the supporting side of said flat rigid support and of said cushioning material is angled relative to said remainder of said supporting side of said flat rigid support and said cushioning material by 75-90°, such that said superior portion is parallel to said horizontal.

4. The device according to claim 1, characterized in that, through assemblage of said flat rigid support with said frame supplied with wheels, said supporting side of said flat rigid support and of said cushioning material takes an inclination of 75-90° compared to the horizontal.

5. The device according to claim 1, characterized in that said frame is a frame of a stroller.

6. The device according to claim 2, characterized in that, through assemblage of said flat rigid support with said frame supplied with wheels, said supporting side of said flat rigid support and of said cushioning material takes an inclination of 75-90° compared to the horizontal.

7. The device according to claim 3, characterized in that, through assemblage of said flat rigid support with said frame supplied with wheels, said supporting side of said flat rigid support and of said cushioning material takes an inclination of 75-90° compared to the horizontal.

8. The device according to claim 2, characterized in that said frame is a frame of a stroller.

9. The device according to claim 3, characterized in that said frame is a frame of a stroller.

10. The device according to claim 4, characterized in that said frame is a frame of a stroller.

11. The device according to claim 6, characterized in that said frame is a frame of a stroller.

12. The device according to claim 7, characterized in that said frame is a frame of a stroller.

13. The device according to claim 1, wherein said side bands are tied to said flat rigid support at a distance sufficient from said lower portion to allow passage of legs of said baby between said lower portion and said side bands.

14. The device according to claim 1, wherein said upper bands are tied to said flat rigid support so as to enable placement of said baby in and removal of said baby from said space.

15. The device according to claim 14, wherein a maximal distance between said back rest and said cushioning material is defined by a length of said upper bands when said upper bands are tied to said flat rigid support.

16. The device according to claim 1, wherein said sling further includes:

side bands located on either side of a central portion of said backrest and tied to said flat rigid support at a distance sufficient from said lower portion to allow passage of legs of said baby between said lower portion and said side bands; and upper bands located on either side of an upper portion of said backrest, and adapted to be tied to said flat rigid support thereby to support said baby in said sling, and to be untied from said flat rigid support so as to enable placement of said baby in and removal of said baby from said space, and wherein a distance between said side bands and said upper bands is adapted to enable passage of arms of said baby therebetween.

17. The device according to claim 1, wherein a bottom portion of said flat rigid support forms a continuous plane with said flat rigid support, and is not curved relative thereto.

18. The device according to claim 1, wherein said lower portion of the sling is provided with mechanisms to adjust its height.

19. The device according to claim 2, wherein said superior portion is curved.

* * * * *